United States Patent [19]

Sisti et al.

[11] 4,343,766

[45] Aug. 10, 1982

[54] DEVICE FOR SAMPLE PICKUP AND WASHING

[75] Inventors: Giorgio Sisti, Melzo; Bruno Tosi, Carate Brianza; Adriano Trisciani, Monza, all of Italy

[73] Assignee: Carlo Erba Strumentazione S.p.A., Italy

[21] Appl. No.: 239,175

[22] Filed: Mar. 2, 1981

[30] Foreign Application Priority Data

Mar. 7, 1980 [IT] Italy .................................. 20413 A/80

[51] Int. Cl.³ .......................... G01N 1/12; G01N 1/14
[52] U.S. Cl. ................................... 422/63; 73/864.21; 422/64; 422/100
[58] Field of Search ........................ 422/100, 64, 63; 73/425.6, 423 A, 864.21

[56] References Cited

U.S. PATENT DOCUMENTS

| | | | |
|---|---|---|---|
| 3,081,158 | 3/1963 | Winter | 422/100 X |
| 3,858,450 | 1/1975 | Jones | 422/100 X |
| 3,915,651 | 10/1975 | Nishi | 422/100 X |
| 4,228,831 | 10/1980 | Kerns | 73/423 A |
| 4,235,840 | 11/1980 | Mendoza et al. | 422/64 |
| 4,276,260 | 6/1981 | Drbal et al. | 422/64 X |

FOREIGN PATENT DOCUMENTS 1361725 7/1974 United Kingdom .
1454767 11/1976 United Kingdom .

Primary Examiner—Ronald E. Serwin
Attorney, Agent, or Firm—Lerner, David, Littenberg & Samuel

[57] ABSTRACT

The invention concerns a device for picking up liquid samples to be analyzed, especially in automatic samplers, said device comprising a needle connected to a sucking pump and supported by a support which moves said needle downwards to pick up the sample from a vial containing same and upwards from said vial. In order to perform a washing step after one aspiration and before the subsequent one, the needle support is designed to perform an oscillating movement when the support is in its upward position with respect to the vial. The oscillating movement is performed by the cooperation of cam means and a control rod having at least a pivot axis controlling the alternative movements. The oscillating movement makes the needle plunge into a sidewardly positioned trough containing a washing liquid.

11 Claims, 8 Drawing Figures

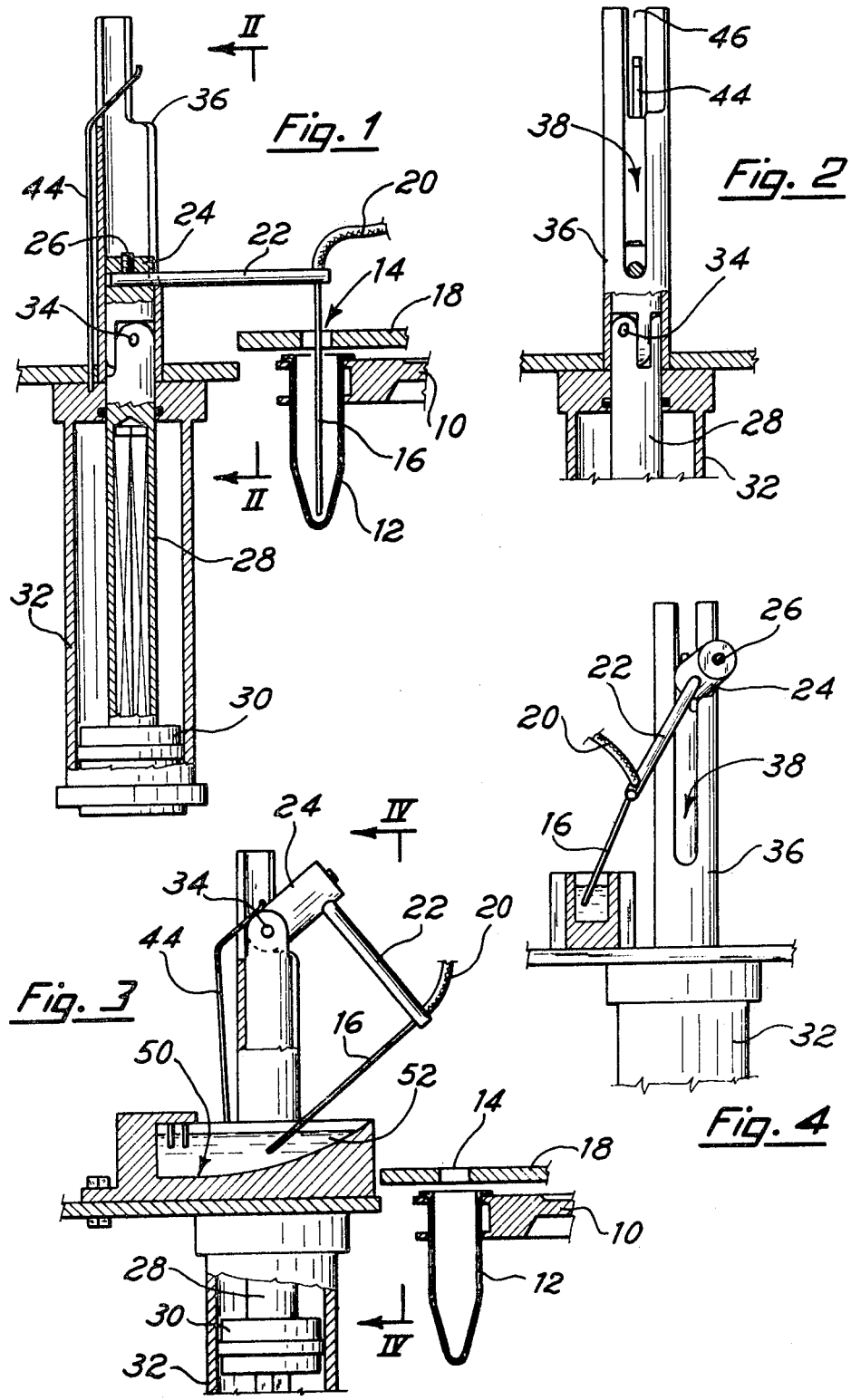

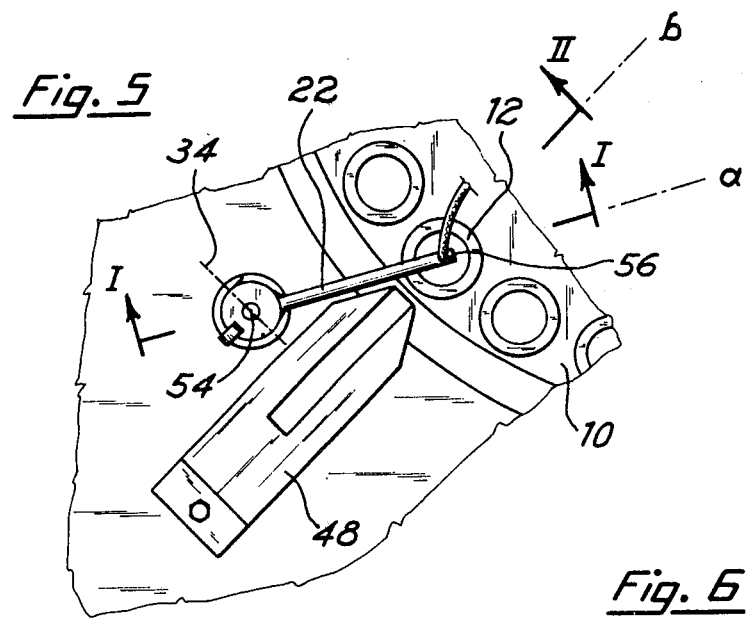
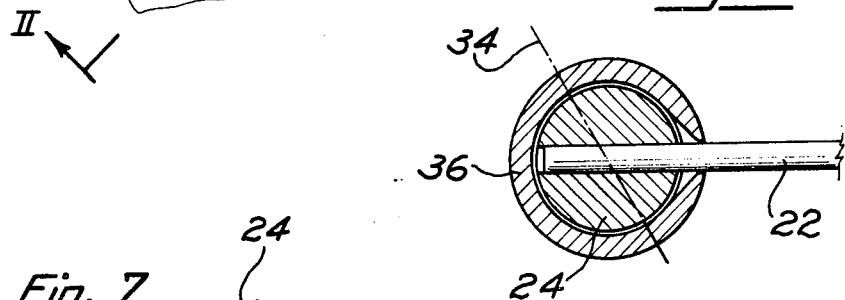
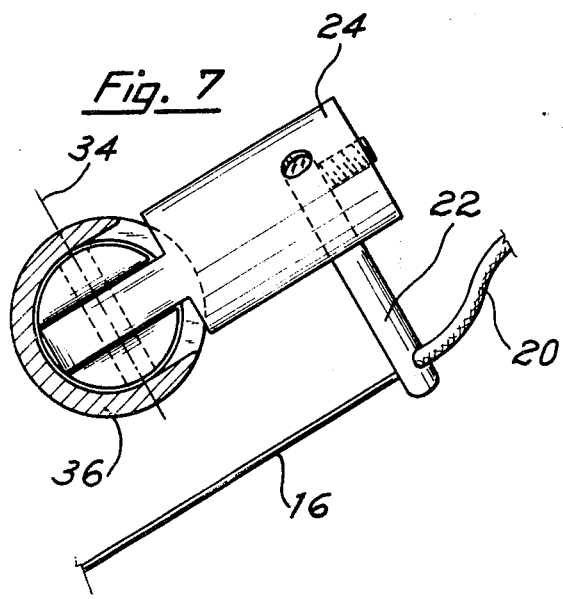
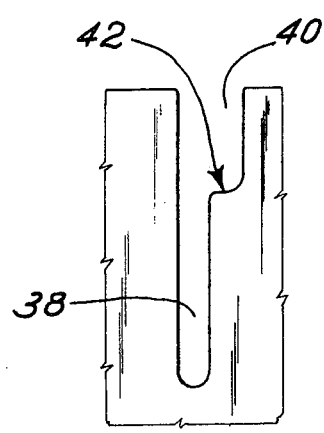

DEVICE FOR SAMPLE PICKUP AND WASHING

BACKGROUND OF THE INVENTION

This invention concerns a device designed to pick-up samples to be analyzed, especially in automatic samplers. The sample pick-up device comprises, in a way known in itself, an aspiration needle connected to a sucking pump and supported by a support. The support controls the axial downwards and upwards alternative movements of the needle for its introduction into a sample vial placed in a sampling position and for removal of the needle from the vial, respectively. At the end of each aspiration, the needle is moved to a position where it sucks a washing liquid from a trough placed by the side of the sample vial.

DESCRIPTION OF THE PRIOR ART

Automatic samplers of the type above defined are well known and generally work in cooperation with a disc carrying a series of vials in which liquid samples are generally placed. The vials are in turn moved into a position or station where the sample is picked up to be injected into the analytical instruments. The sample aspiration is carried out, as already said, by means of a needle which performs downwards and upwards alternative movements when the vial is in the sampling position. The needle must then be submitted to a washing after each aspiration and before the subsequent one. For this reason, in the known samplers, especially of the automatic type, the needle is supported by a transverse small bar, in particular perpendicular to the needle axis. The movements of the transverse bar are in turn controlled by a control rod, in particular a piston rod, which moves in a manner parallel to the needle axis upwards and downwards, respectively. To perform washing after each aspiration, the supporting rod of the needle is rotated by a given angle around its own axis, so as to bring the needle to a position outside the sample-holding disc and above a trough placed sideways in a fixed position. The needle is then plunged into the trough by another movement of the control rod.

This control system for the sample needle movements, however, shows some drawbacks. Firstly, this control system is mechanically complex due to the fact that the control rod must not only perform upwards and downwards alternative movements, but must also rotate around its own axis, according to a predetermined sequence. Moreover, the performance of a complete cycle of movements, namely, lowering the needle into the sample vial, lifting the needle itself, rotating the needle around the control rod, lowering the needle into the washing trough, lifting the needle from the trough and finally, rotating the needle to a position aligned with the subsequent sample vial, is relatively time consuming and negatively affects the analysis rapidity. Therefore, the total efficiency of the whole equipment is negatively affected. Finally, the complexity of mechanics and above-described movements involves a relatively reduced reliability in the control of the needle movements, with consequent possibility of wrong movements or wrong positionings of the needle. Such wrong movements or positionings may cause breaking of the needle itself and errors in the analysis of certain samples.

SUMMARY OF THE INVENTION

Accordingly, an object of the present invention is to provide a device of the mentioned type and for the mentioned operations, which allows avoidance of the above drawbacks of the known devices of this type. Particularly, it is an object of the invention to provide a device which allows the performance of the whole working cycle of sample aspiration and needle washing by means of control means having an extremely simplified mechanical structure with quicker operation and higher reliability.

Essentially, according to the invention, said objects are achieved by a needle support which has a mechanical component pivoted to the rod controlling the movements of the needle support, which rod is moved in the two directions parallel to the direction of the needle movement during sampling. Also, a guide is provided for said support component, which guide is capable of guiding the support component towards said directions for the major part of the control rod upward and downward run. Moreover, said guide has a cam area capable of providing a rotation of the support component around its own pivoting axis and a subsequent sideward movement of the needle into the washing trough, during the final upward portion of the control rod upward movement. The guide and cam area also carry the support component, together with the needle, back to the sampling conditions, during the initial downward movement portion of the control rod downward movement.

BRIEF DESCRIPTION OF THE DRAWINGS

FIG. 1 is a cross-sectional view of the device according to the invention, along a vertical plane comprising both the axis of the sample vial during sampling operation and the axis of the needle control rod, which is parallel to the former one.

FIG. 2 is a cross-sectional view according to the line II—II of FIG. 1.

FIG. 3 is a cross-sectional view according to a vertical plane comprising both the longitudinal axis of the washing trough and the axis of the vial during the sampling stage, said view showing the device during its washing stage.

FIG. 4 is a cross-sectional view according to the line IV—IV of FIG. 3.

FIG. 5 is a schematic plan view of the device during the sampling stage, said figure indicating by I—I and II—II the sectional lines of FIGS. 1 and 2, respectively.

FIG. 6 is a partial cross-sectional view according to a plane perpendicular to the axis of the device control rod and showing the device in its sampling position.

FIG. 7 is a cross-sectional view corresponding to that of FIG. 6 and showing the device in its washing position.

FIG. 8 is a planar development view of the guide and in particular of the seat and cam shape provided on same.

DESCRIPTION OF THE PREFERRED EMBODIMENT

With reference to the drawings an automatic sampler includes, in a way known in itself, a disc 10 which is intermittently rotated so as to carry each one of a series of vials 12 to a position of aspiration or sampling indicated by the reference 14.

For the aspiration of the sample contained in each vial 12, a needle 16 is plunged into the vial itself through an opening in a plate 18, so that the sample may be picked up by means of a sucking pump connected through a channel 20 to the needle 16.

The needle 16 is supported by a transversal small bar 22, generally perpendicular to the needle itself. The needle support is constituted of the needle and a small block 24 to which said small bar 22 is fixed by means of a dowel 26. Said small block 24 is vertically moved by means of a rod 28, for instance, controlled by a piston 30 movable inside a cylinder 32 and in turn controlled by suitable means (not shown). The small block 24 is controlled in such a way as to plunge the needle 16 into vial 12, as illustrated in FIG. 1, and to lift the needle above the plate 18, so as to allow both the rotation of disc 10 to carry another vial 12 below the needle, and a movement of the needle to a washing position.

According to the invention, said small block 24 is connected to the rod 28 by means of a horizontally positioned pivot 34. The movements of the pivot are controlled by means of a tube 36 having a longitudinal slot for the passage of the supporting bar 22. In its upper part and in continuation to the slot 38, the tube 36 has a widened opening 40, the edge of which is connected to the wall of slot 38 by means of a cam shaping 42. The widened opening allows rotation of the small block 24 around its own pivot 34, until the small block reaches the position illustrated in FIGS. 3, 4 and 7. This rotation of the small block 24 around the pivot 34 is made easier by the presence of a flat spring 44 cooperating with the tube 36 and capable of acting on the small block 24, when the latter reaches its upper end position, through a slit 46 in the tube 36 itself.

As can be particularly noticed in FIG. 5, a washing trough 48 is placed by the side of the control rod 28. The washing trough 48 has an essentially elongated configuration, with an approximately arc-shaped seat 50 for a washing liquid 52. In order that the rotation around pivot 34 (which is schematically shown in FIGS. 5, 6 and 7 by its own axis) can allow the needle 16 to plunge into the trough 48, it is essential to have a well given reciprocal geometrical position of the pivot 34 and small bar 22, as well as the other device components. As can be seen particularly in FIGS. 5 and 6, the axis 34 forms an angle different from 90° with the small bar 22. As shown in more detail in the plan view of FIG. 5, the small bar 22 constitutes a connection between the axis 54 of control rod 28 and the axis 56 of needle 16, when the needle is in its sampling position. This connection forms a first alignment designated by "a" in FIG. 5. The trough 48 has a longitudinal shape along a second alignment designated by "b" in FIG. 5. This second alignment passes through the axis 56 and forms a given acute angle with the first alignment "a". In order that the needle may penetrate into the trough 48, the axis 34 must form with the second alignment "b" an angle of 90°. In this way, when the small block 24 is free to rotate around the pivot 34, it causes a rotation of a small bar 22 around said axis and therefore a rotation of the point of needle 16 along a centered-arc trajectory which leads said point into the trough 48.

Once the washing has been performed, with methods known in themselves, it is sufficient to move again the control rod 28 to its lower limit position so that, during the first part of its run, the cam shaping 42 determines a straightening of block 24. Therefore, the needle 16 reaches a position aligned with the sampling position above the vial 12, in which position the needle is ready to be further lowered during the second part of the run of rod 28, until it penetrates into the vial 12. The above clearly shows that, for each cycle of sample aspiration and needle washing, the control rod movements are reduced to a single downwards and upwards movement of same, with an automatic control of the needle movement as it penetrates into the washing trough, in correspondence to the final upper section of the control rod run. The needle then returns to its position in alignment with the sample vial for sampling during the initial part of the control rod downwards run. This allows not only simplification of the mechanical structure of the device, but also provides reliability in the movements and operations of same and increases the speed of the whole working cycle. Consequently, the productivity of the equipment to which the device itself is applied is increased.

It is to be understood that the above shown embodiment can be modified in the details of realization of same, without departing from the spirit and scope of the present invention.

We claim:

1. A device for automatic sample pick-up and washing, said device comprising a washing trough for washing fluid; a control rod reciprocally movable in a first direction between a control rod sampling position and a control rod washing position; a support component supporting a needle fluidically connected to a suction pump; pivot means mounted with respect to said control rod and said support component for pivoting said support component about an axis along a second direction different from said first direction so that, as the control rod moves to and from its washing position, said support component pivots to and from a support component washing position to move at least the tip of said needle into and out of said washing trough; and means for moving said control rod between said control rod sampling and washing positions to provide a support component sampling position and said support component washing position.

2. A device according to claim 1, further comprising guide means for guiding said support component between said support component sampling and washing positions and for controlling the rotation of said support component into and out of said support component washing position.

3. A device according to claim 1 or 2, wherein said first direction is substantially parallel to the direction of the needle when the needle is in its sampling position.

4. A device according to claim 1 or 2, wherein said first direction is substantially vertical and wherein said reciprocal movement is upward and downward.

5. A device according to claim 2, wherein said guide means comprises a cam surface for controlling rotation of said pivot means about said axis.

6. A device according to claim 5, wherein said pivot means comprises a shaped block which is connected to said control rod, which is pivotable about said axis; wherein said support component comprises a transversal bar supporting said needle; and wherein said guide means comprises a tube coaxial with said control rod, said tube having a shape matching said shaped block, having a slot therein for passage of said transversal bar therethrough, and having a shaped opening in its upper section connected to said slot which shaped opening is sufficiently large to allow rotation of said shaped block around said pivot axis.

7. A device according to claim 6, wherein the angle between said transversal bar supporting said needle and said pivot axis is less than 90 degrees when in a horizontal plane projection.

8. A device according to claim 7, wherein a sample vial and said washing trough are placed along a first horizontal direction; wherein the vertical axis of said sample vial, the horizontal axis of the supporting transversal bar when it is in its sampling position, and the vertical axis of the guide tube are placed along a second horizontal direction; wherein said first horizontal direction and said second horizontal direction form an angle in correspondence to the vertical axis of said sample vial; and wherein said pivot axis of said shaped block is horizontal, crosses said axis of said guide tube, and is perpendicular to said first horizontal direction.

9. A device according to claim 8, wherein said transversal bar is perpendicular to said needle and to said guide tube axis in a vertical plane, when said transversal bar is in its sampling position.

10. A device according to claim 6, 7, or 8, wherein said guide means includes at least one spring associated with said guide tube, said spring pushing said shaped block towards its rotated position when said control rod is in its washing position in said tube.

11. A device according to claim 10, wherein said washing trough has an elongated configuration along said first horizontal direction and has an arcuate section matching the arc trajectory of the tip of the needle as the support component pivots to and from the support component washing position.

* * * * *